United States Patent
Vitaris

(10) Patent No.: US 8,152,785 B2
(45) Date of Patent: Apr. 10, 2012

(54) VACUUM PORT FOR VACUUM WOUND THERAPY

(75) Inventor: Bethany A. Vitaris, Worcester, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 406 days.

(21) Appl. No.: 12/402,893

(22) Filed: Mar. 12, 2009

(65) Prior Publication Data

US 2009/0234307 A1 Sep. 17, 2009

Related U.S. Application Data

(60) Provisional application No. 61/036,275, filed on Mar. 13, 2008.

(51) Int. Cl.
*A61F 13/00* (2006.01)
*A61M 27/00* (2006.01)
*A61M 1/00* (2006.01)

(52) U.S. Cl. ......... 604/304; 604/543; 604/317; 604/319

(58) Field of Classification Search .................. 604/317, 604/304, 319, 543, 541
See application file for complete search history.

(56) References Cited

U.S. PATENT DOCUMENTS

| | | | |
|---|---|---|---|
| 3,367,332 A | 2/1968 | Groves |
| 3,486,504 A | 12/1969 | Austin, Jr. |
| 3,572,340 A | 3/1971 | Lloyd et al. |
| 3,712,298 A | 1/1973 | Snowdon et al. |
| 3,809,086 A | 5/1974 | Schachet et al. |
| 3,874,387 A | 4/1975 | Barbieri |
| 4,080,970 A | 3/1978 | Miller |
| 4,112,947 A | 9/1978 | Nehring |
| 4,112,949 A | 9/1978 | Rosenthal et al. |
| 4,136,696 A | 1/1979 | Nehring |
| 4,266,545 A | 5/1981 | Moss |
| 4,382,441 A | 5/1983 | Svedman |
| 4,524,064 A | 6/1985 | Nambu |
| 4,743,232 A | 5/1988 | Kruger |
| 4,969,880 A | 11/1990 | Zamierowski |
| 4,990,137 A | 2/1991 | Graham |
| 4,997,438 A | 3/1991 | Nipper |

(Continued)

FOREIGN PATENT DOCUMENTS

DE 41 11 122 A1 4/1993

(Continued)

OTHER PUBLICATIONS

International Search Report, Application No. PCT/US09/37133, dated May 18, 2009.

(Continued)

*Primary Examiner* — Leslie Deak
*Assistant Examiner* — Susan Su
(74) *Attorney, Agent, or Firm* — Elias Domingo, Esq.

(57) ABSTRACT

The present disclosure describes a dressing for use in a vacuum wound therapy procedure to promote healing of a wound. The dressing includes a cover layer for positioning over a wound to define a reservoir in which a reduced pressure may be maintained over the wound. A portal member is mounted relative to the cover layer and defines a fluid passage for fluid coupling with a reduced pressure supply conduit for creating the reduced pressure within the reservoir. A filter screen is mounted relative to the fluid passage and is dimensioned to minimize passage of tissue particles of predetermined dimension through the fluid passage of the portal member.

12 Claims, 7 Drawing Sheets

U.S. PATENT DOCUMENTS

| | | | |
|---|---|---|---|
| 5,071,409 A | 12/1991 | Rosenberg | |
| 5,100,395 A | 3/1992 | Rosenberg | |
| 5,100,396 A | 3/1992 | Zamierowski | |
| 5,106,629 A | 4/1992 | Cartmell et al. | |
| 5,141,503 A | 8/1992 | Sewell, Jr. | |
| 5,149,331 A | 9/1992 | Ferdman et al. | |
| 5,152,757 A | 10/1992 | Eriksson | |
| 5,160,322 A * | 11/1992 | Scheremet et al. | 604/122 |
| 5,176,663 A | 1/1993 | Svedman et al. | |
| 5,178,157 A | 1/1993 | Fanlo | |
| 5,195,977 A | 3/1993 | Pollitt | |
| 5,261,893 A | 11/1993 | Zamierowski | |
| 5,263,922 A | 11/1993 | Sova et al. | |
| 5,431,633 A * | 7/1995 | Fury | 604/122 |
| D364,679 S | 11/1995 | Heaton et al. | |
| 5,484,427 A | 1/1996 | Gibbons | |
| 5,527,293 A | 6/1996 | Zamierowski | |
| 5,536,233 A | 7/1996 | Khouri | |
| 5,549,584 A | 8/1996 | Gross | |
| 5,588,958 A | 12/1996 | Cunningham et al. | |
| 5,636,643 A | 6/1997 | Argenta et al. | |
| 5,645,081 A | 7/1997 | Argenta et al. | |
| 5,678,564 A | 10/1997 | Lawrence et al. | |
| 5,701,917 A | 12/1997 | Khouri | |
| 5,733,305 A | 3/1998 | Fleischmann | |
| 5,840,049 A | 11/1998 | Tumey et al. | |
| 5,911,222 A | 6/1999 | Lawrence et al. | |
| 5,944,703 A | 8/1999 | Dixon et al. | |
| 6,010,524 A | 1/2000 | Fleischmann | |
| 6,071,267 A | 6/2000 | Zamierowski | |
| 6,117,111 A | 9/2000 | Fleischmann | |
| 6,135,116 A | 10/2000 | Vogel et al. | |
| D434,150 S | 11/2000 | Tumey et al. | |
| 6,142,982 A | 11/2000 | Hunt et al. | |
| 6,174,306 B1 | 1/2001 | Fleischmann | |
| 6,203,563 B1 | 3/2001 | Fernandez | |
| 6,261,276 B1 | 7/2001 | Reitsma | |
| 6,325,788 B1 | 12/2001 | McKay | |
| 6,345,623 B1 | 2/2002 | Heaton et al. | |
| 6,348,423 B1 | 2/2002 | Griffiths et al. | |
| 6,398,767 B1 | 6/2002 | Fleischmann | |
| 6,406,447 B1 | 6/2002 | Thrash et al. | |
| 6,420,622 B1 | 7/2002 | Johnston et al. | |
| 6,458,109 B1 | 10/2002 | Henley et al. | |
| 6,488,643 B1 | 12/2002 | Tumey et al. | |
| 6,500,112 B1 | 12/2002 | Khouri | |
| D469,175 S | 1/2003 | Hall et al. | |
| D469,176 S | 1/2003 | Hall et al. | |
| 6,520,982 B1 | 2/2003 | Boynton et al. | |
| 6,553,998 B2 | 4/2003 | Heaton et al. | |
| D475,134 S | 5/2003 | Randolph | |
| 6,557,704 B1 | 5/2003 | Randolph | |
| D478,659 S | 8/2003 | Hall et al. | |
| 6,607,495 B1 | 8/2003 | Skalak et al. | |
| 6,626,891 B2 | 9/2003 | Ohmstede | |
| 6,648,862 B2 | 11/2003 | Watson | |
| 6,685,681 B2 | 2/2004 | Lockwood et al. | |
| 6,695,823 B1 | 2/2004 | Lina et al. | |
| 6,695,824 B2 | 2/2004 | Howard et al. | |
| D488,558 S | 4/2004 | Hall | |
| 6,752,794 B2 | 6/2004 | Lockwood et al. | |
| 6,755,807 B2 | 6/2004 | Risk, Jr. et al. | |
| 6,764,462 B2 | 7/2004 | Risk, Jr. et al. | |
| 6,767,334 B1 | 7/2004 | Randolph | |
| 6,800,074 B2 | 10/2004 | Henley et al. | |
| 6,814,079 B2 | 11/2004 | Heaton et al. | |
| 6,824,533 B2 | 11/2004 | Risk, Jr. et al. | |
| 6,855,135 B2 | 2/2005 | Lockwood et al. | |
| 6,856,821 B2 | 2/2005 | Johnson | |
| 6,887,228 B2 | 5/2005 | McKay | |
| 6,887,263 B2 | 5/2005 | Bleam et al. | |
| 6,936,037 B2 | 8/2005 | Bubb et al. | |
| 6,942,633 B2 | 9/2005 | Odland | |
| 6,942,634 B2 | 9/2005 | Odland | |
| 6,951,553 B2 | 10/2005 | Bubb et al. | |
| 6,960,181 B2 | 11/2005 | Stevens | |
| 6,979,324 B2 | 12/2005 | Bybordi et al. | |
| 6,994,702 B1 | 2/2006 | Johnson | |
| 7,022,113 B2 | 4/2006 | Lockwood et al. | |
| 7,037,254 B2 | 5/2006 | O'Connor et al. | |
| 7,052,167 B2 | 5/2006 | Vanderschuit | |
| 7,070,584 B2 | 7/2006 | Johnson et al. | |
| 7,077,832 B2 | 7/2006 | Fleischmann | |
| 7,108,683 B2 | 9/2006 | Zamierowski | |
| 7,117,869 B2 | 10/2006 | Heaton et al. | |
| 7,128,719 B2 | 10/2006 | Rosenberg | |
| 7,128,735 B2 | 10/2006 | Weston | |
| 7,144,390 B1 | 12/2006 | Hannigan et al. | |
| 7,169,151 B1 | 1/2007 | Lytinas | |
| 7,182,758 B2 | 2/2007 | McCraw | |
| 7,195,624 B2 * | 3/2007 | Lockwood et al. | 604/543 |
| 7,198,046 B1 | 4/2007 | Argenta et al. | |
| 7,214,202 B1 | 5/2007 | Vogel et al. | |
| 7,216,651 B2 | 5/2007 | Argenta et al. | |
| D544,092 S | 6/2007 | Lewis | |
| 7,273,054 B2 | 9/2007 | Heaton et al. | |
| 7,276,051 B1 | 10/2007 | Henley et al. | |
| 7,279,612 B1 | 10/2007 | Heaton et al. | |
| 7,316,672 B1 | 1/2008 | Hunt et al. | |
| D565,177 S | 3/2008 | Locke et al. | |
| 7,338,482 B2 | 3/2008 | Lockwood et al. | |
| 7,351,250 B2 | 4/2008 | Zamierowski | |
| 7,361,184 B2 | 4/2008 | Joshi | |
| 7,381,211 B2 | 6/2008 | Zamierowski | |
| 7,381,859 B2 | 6/2008 | Hunt et al. | |
| 7,396,345 B2 | 7/2008 | Knighton et al. | |
| 7,410,495 B2 | 8/2008 | Zamierowski | |
| 7,413,570 B2 | 8/2008 | Zamierowski | |
| 7,413,571 B2 | 8/2008 | Zamierowski | |
| 7,422,576 B2 | 9/2008 | Boynton et al. | |
| 7,429,687 B2 * | 9/2008 | Kauth et al. | 602/58 |
| 7,776,028 B2 * | 8/2010 | Miller et al. | 604/543 |
| 7,846,141 B2 * | 12/2010 | Weston | 604/313 |
| 2001/0031943 A1 | 10/2001 | Urie | |
| 2001/0043943 A1 | 11/2001 | Coffey | |
| 2002/0016577 A1 | 2/2002 | Ohmstede | |
| 2002/0143286 A1 | 10/2002 | Tumey | |
| 2002/0151836 A1 | 10/2002 | Burden | |
| 2003/0040687 A1 * | 2/2003 | Boynton et al. | 601/6 |
| 2003/0093041 A1 | 5/2003 | Risk, Jr. et al. | |
| 2003/0208149 A1 | 11/2003 | Coffey | |
| 2003/0212357 A1 | 11/2003 | Pace | |
| 2003/0212359 A1 | 11/2003 | Butler | |
| 2003/0219469 A1 | 11/2003 | Johnson et al. | |
| 2004/0006319 A1 | 1/2004 | Lina et al. | |
| 2004/0030304 A1 | 2/2004 | Hunt et al. | |
| 2004/0039415 A1 | 2/2004 | Zamierowski | |
| 2004/0064132 A1 | 4/2004 | Boehringer et al. | |
| 2004/0073151 A1 | 4/2004 | Weston | |
| 2004/0093026 A1 | 5/2004 | Weidenhagen et al. | |
| 2004/0122434 A1 | 6/2004 | Argenta et al. | |
| 2004/0193218 A1 | 9/2004 | Butler | |
| 2004/0241213 A1 | 12/2004 | Bray | |
| 2004/0243073 A1 * | 12/2004 | Lockwood et al. | 604/313 |
| 2005/0010153 A1 | 1/2005 | Lockwood et al. | |
| 2005/0020955 A1 | 1/2005 | Sanders et al. | |
| 2005/0070835 A1 | 3/2005 | Joshi | |
| 2005/0070858 A1 | 3/2005 | Lockwood et al. | |
| 2005/0085795 A1 | 4/2005 | Lockwood et al. | |
| 2005/0090787 A1 | 4/2005 | Risk, Jr. et al. | |
| 2005/0177190 A1 | 8/2005 | Zamierowski | |
| 2005/0182445 A1 | 8/2005 | Zamierowski | |
| 2005/0222527 A1 | 10/2005 | Miller et al. | |
| 2005/0222544 A1 | 10/2005 | Weston | |
| 2005/0261642 A1 | 11/2005 | Weston | |
| 2005/0261643 A1 | 11/2005 | Bybordi et al. | |
| 2006/0015087 A1 | 1/2006 | Risk, Jr. et al. | |
| 2006/0025727 A1 | 2/2006 | Boehringer et al. | |
| 2006/0039742 A1 | 2/2006 | Cable, Jr. et al. | |
| 2006/0041247 A1 | 2/2006 | Petrosenko et al. | |
| 2006/0079852 A1 | 4/2006 | Bubb et al. | |
| 2006/0100586 A1 | 5/2006 | Karpowicz et al. | |
| 2006/0100594 A1 | 5/2006 | Adams et al. | |
| 2006/0116620 A1 | 6/2006 | Oyaski | |
| 2006/0149170 A1 | 7/2006 | Boynton et al. | |
| 2007/0005028 A1 | 1/2007 | Risk, Jr. et al. | |
| 2007/0014837 A1 | 1/2007 | Johnson et al. | |

| | | | |
|---|---|---|---|
| 2007/0021697 A1 | 1/2007 | Ginther et al. | |
| 2007/0027414 A1* | 2/2007 | Hoffman et al. | 602/2 |
| 2007/0032754 A1 | 2/2007 | Walsh | |
| 2007/0032755 A1 | 2/2007 | Walsh | |
| 2007/0032778 A1 | 2/2007 | Heaton et al. | |
| 2007/0055209 A1 | 3/2007 | Patel et al. | |
| 2007/0066946 A1 | 3/2007 | Haggstrom et al. | |
| 2007/0078366 A1 | 4/2007 | Haggstrom et al. | |
| 2007/0167927 A1 | 7/2007 | Hunt et al. | |
| 2007/0179460 A1 | 8/2007 | Adahan | |
| 2007/0185426 A1 | 8/2007 | Ambrosio et al. | |
| 2007/0225663 A1 | 9/2007 | Watt et al. | |
| 2007/0265586 A1* | 11/2007 | Joshi et al. | 604/313 |
| 2008/0071235 A1 | 3/2008 | Locke et al. | |
| 2008/0200857 A1 | 8/2008 | Lawhorn | |
| 2008/0200906 A1 | 8/2008 | Sanders et al. | |
| 2008/0208147 A1 | 8/2008 | Argenta et al. | |
| 2008/0234641 A1 | 9/2008 | Locke et al. | |
| 2008/0294147 A1* | 11/2008 | Radl et al. | 604/543 |
| 2008/0300555 A1* | 12/2008 | Olson et al. | 604/313 |

FOREIGN PATENT DOCUMENTS

| | | |
|---|---|---|
| DE | 295 04 378 U1 | 10/1995 |
| EP | 0 020 662 B1 | 7/1984 |
| EP | 0 358 302 | 3/1990 |
| EP | 0 853 950 B1 | 10/2002 |
| GB | 1 549 756 | 3/1977 |
| GB | 2 195 255 A | 4/1988 |
| GB | 2 235 877 A | 3/1991 |
| SU | 1762940 | 1/1989 |
| WO | 80/01139 | 6/1980 |
| WO | 80/02182 | 10/1980 |
| WO | 84/01904 | 5/1984 |
| WO | 89/05133 | 6/1989 |
| WO | 90/11795 | 10/1990 |
| WO | 92/19313 | 11/1992 |
| WO | 96/05873 | 2/1996 |
| WO | 9605873 | 2/1996 |
| WO | 03057307 | 7/2003 |
| WO | 03101508 | 12/2003 |
| WO | 2005009488 | 2/2005 |

OTHER PUBLICATIONS

Meyer, M.D., et al., "In Surgery, Medicine and the Specialties a Manual of its Practical Application", Bier's Hyperemic Treatment, Second Revised Edition, W.B. Saunders Company, 1909.

Jeter, Katherine F., et al., "Managing Draining Wounds and Fistulae: New and Established Methods", Chronic Wound Care, 1990, pp. 240-246.

Chariker, M. E. et al. (eds), "Effective Management of Incisional and Cutaneous Fistulae with Closed Suction Wound Drainage," Contemporary Surgery, vol. 34, Jun. 1989, pp. 59-63.

B.M. Kostiuchenok, et al., "The Vacuum Effect in the Surgical Treatment of Purulent Wounds," Russian Journal: Vestnik Khirurgii, Sep. 1986 (18-21).

Y.N. Usupov, et al., "Active Wound Drainage," Russian Journal: Vestnik Khirugii, Apr. 1987 (42-45).

Yu A. Davydov, et al., "Concepts for Clinical Biological Management of the Wound Process in the Treatment of Purulent Wounds Using Vacuum Therapy," Vestnik Khirugii, Feb. 1991, 132-135).

N. A. Bagautdinov (Kazan), "Variant of External Vacuum Aspiration in the Treatment of Purulent Diseases of Soft Tissues," UDC 616-002.36 (94-96).

Chardack, et al., "Experimental studies on Synthetic Substitutes for Skin and Their Use in the Treatment of Burns," vol. 155, No. 1 (128-136).

Gorica Zivadinovic, et al., "Vacuum Therapy in the Treatment of Peripheral Blood Vessels," Conference Papers of the 5th Timok Medical Days, Majdanpek, 1986 (161-164).

Ryosuke Fujimoro, M.D., et al., "Sponge Fixation Method for Treatment of Early Scars," From the Department of Dermatology in the Faculty Medicine, Kyoto University, vol. 42, No. 4, Oct. 1968 (323-326).

W. Fleischmann, et al., Vacuum Sealing: Indication, Technique and Results, Emr J Orthop Surg Tramatol (1995) 5:37-40.

Sherry Stoll, "Energetic Remedies—Cupping: Healing Within a Vacuum," https://www.suite101.com/article.cfm/energetic)remedies/74531, Apr. 13, 2005.

Mulder, G.D, et al., "Clinicians' Pocket Guide to Chronic Wound Repair," Wound Healing Publications Second Edition, 1991.

Yu A. Davydov, et al., "Vacuum Therapy in the Treatment of Purulent Lactation Mastitis," Russian Journal: Vesnik Khirurgii, Sep. 1986 (66-70).

Yu A. Davydov, et al., "Bacteriological and Cytological Assessment of Vacuum Therapy of Purulent Wounds", Vestnik Khirurgii, Oct. 1988 (48-52).

W. Fleischmann, "Vacuum Sealing for Treatment of Problematical Wounds", University Surgical Clinic and Polyclinic—Accident Surgery Department, WundForum Spezial—IHW 94.

Göran Sandén, M.D., et al., "*Staphylococcal* Wound Infection in the Pig: Part II. Innoculation, Quantification of Bacteria, and Reproducibility," Annals of Plastic Surgery, vol. 23, No. 3, Sep. 1989, (219-223).

Björn, et al., "Irrigation Treatment in Split-thickness Skin Grafting of Intractable Leg Ulcers," Scand J Plast Reconstr Surg 19: 211-213, 1985.

Paul Svedman, et al., "*Staphylococcal* Wound Infection in the Pig: Part I. Course," Annals of Plastic Surgery, vol. 23, No. 3, Sep. 1989 (212-218).

Paul Svedman, "A Dressing Allowing Continuous Treatment of a Biosurface," IRCS Medical Science: Biomedical Technology; Clinical Medicine; Surgery and Transplantation, 7, 221 (1979).

Paul Svedman, "Irrigation Treatment of Leg Ulcers," The Lancet, Sep. 3, 1983 (532-534).

H. Teder, et al., "Continuous Wound Irrigation in the Pig," Journal of Investigative Surgery, vol. 3 (399-407).

P. Svedman, "A Dressing System Providing Fluid Supply and Suction Drainage Used for Continuous or Intermittent Irrigation," Annals of Plastic Surgery, vol. 17, No. 2, Aug. 1986 (125-133).

Yu A. Davydov, et al., "Vacuum Therapy in treatment of Acute Purulent Diseases of Soft Tissues and Purulent Wounds," Vestnik Khirurgii, (Surgeon's Herald), Medicine Publishers, 1986.

US 6,216,701, 04/2001, Heaton et al. (withdrawn)
US 7,186,244, 03/2007, Hunt et al. (withdrawn)

\* cited by examiner

VACUUM PORT FOR VACUUM WOUND THERAPY

CROSS REFERENCE TO RELATED APPLICATION

This application claims priority to, and the benefit of, U.S. Provisional Application Ser. No. 61/036,275, filed on Mar. 13, 2008 by Vitaris, the entire contents of which are being hereby incorporated by reference herein.

BACKGROUND

1. Technical Field

The present disclosure relates generally to a wound dressing for treating an open wound with a vacuum wound therapy procedure. In particular, the disclosure relates to a wound dressing employing a portal member to establish fluid communication between a fluid conduit and a reservoir over a wound in which a negative pressure may be maintained.

2. Background of Related Art

The body's natural wound healing process is a complex series of events beginning at the moment of injury. Initially the body reacts by delivering proteins and other factors to the wound through the blood stream to minimize the damage. Blood clots to prevent blood loss while cells engulf bacteria and debris to carry it away from the wound site. Next, the body begins to repair itself in a stage of healing often referred to as the proliferate phase. This phase is characterized by the deposition granulation tissue in the wound bed. Granulation tissue provides a base structure over which cells may migrate inwardly from the periphery to close the wound. Finally the process ends as collagen gives strength to new tissue over time often forming a scar.

One technique for promoting the natural healing process, particularly, but not exclusively during the proliferate phase, is known as vacuum wound therapy (VWT). Application of a reduced pressure, e.g. sub-atmospheric, to a localized reservoir over a wound has been found to assist in closing the wound. The reduced pressure may be effective to promote blood flow to the area, to stimulate the formation of granulation tissue and the migration of healthy tissue over the wound by the natural process. Also a reduced pressure may assist in removing fluids exuding from the wound, which may inhibit bacterial growth. This technique has proven effective for chronic or non-healing wounds, but has also been used in for other purposes such as post-operative wound care.

The general VWT protocol provides for the introduction of a filler material into the wound to absorb exudates and promote fluid transport away from the wound bed. The wound filler may comprise such materials as non-reticulated foams, non-woven reinforcements or gauze. The wound and the absorbent wound filler material may then be covered by a flexible cover layer having an adhesive periphery that forms a substantially fluid tight seal with the healthy skin surrounding the wound. The cover layer thus defines a vacuum reservoir over the wound where a reduced pressure may be maintained over time by individual or cyclic evacuation procedures.

An aspect of concern in a VWT treatment is the management of wound fluids drawn from the wound. For example, wound fluids may include large particles, which may tend to clog fluid conduits available for exudate transport and may also inhibit penetration of the reduced pressure to the wound. Also bacteria in the wound fluid may generate an unpleasant odor or may present health risks to patients and clinicians.

Accordingly, a need exists for a dressing including a vacuum port suitable for managing wound fluids in a VWT procedure.

SUMMARY

The present disclosure describes a dressing for use in a vacuum wound therapy procedure to promote healing of a wound. The dressing includes a cover layer for positioning over a wound to define a reservoir in which a reduced pressure may be maintained over the wound. A portal member is mounted relative to the cover layer and defines a fluid passage for fluid coupling with a reduced pressure supply conduit for creating the reduced pressure within the reservoir. A filter screen is mounted relative to the fluid passage and is dimensioned to minimize passage of tissue particles of predetermined dimension through the fluid passage of the portal member.

The filter screen may be integral to the portal member. Alternatively, the filter screen may be a distinct component from the portal member, and the portal member may include a cavity therein to receive the filter screen. The filter screen may be dimensioned to be received within the cavity such that the filter screen is substantially flush with a patient facing underside of the portal member. Alternatively, the filter screen may be dimensioned to be received within the cavity such that the filter screen extends beyond the patient facing underside of the portal member.

The filter screen may include a therapeutic material adapted to control a characteristic of exudate drawn through the fluid passage of the portal member. The therapeutic material may include activated charcoal to control an odor of the exudate, or an antimicrobial to control a bio-burden of the exudate.

The wound dressing may include a treatment element mounted adjacent the filter screen, wherein the treatment element includes a material adapted to control a characteristic of exudate drawn through the fluid passage of the portal member. The material of the treatment element may be adapted to control one of odor and microbials. The wound dressing may include a second filter screen and the treatment element may be secured between first and second filter screens to define an insert for reception into the cavity.

The portal member may include a flange defining an outer surface and a patient surface generally facing the wound, and the fluid passage may extend through the outer surface and the patient surface. The portal member may also include a connector segment for connection to the reduced pressure supply conduit. The flange of the portal member may be secured to the cover layer of the dressing. A negative pressure source may be in fluid communication with the reduced pressure supply conduit.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION OF PREFERRED EMBODIMENTS

Figure 1:
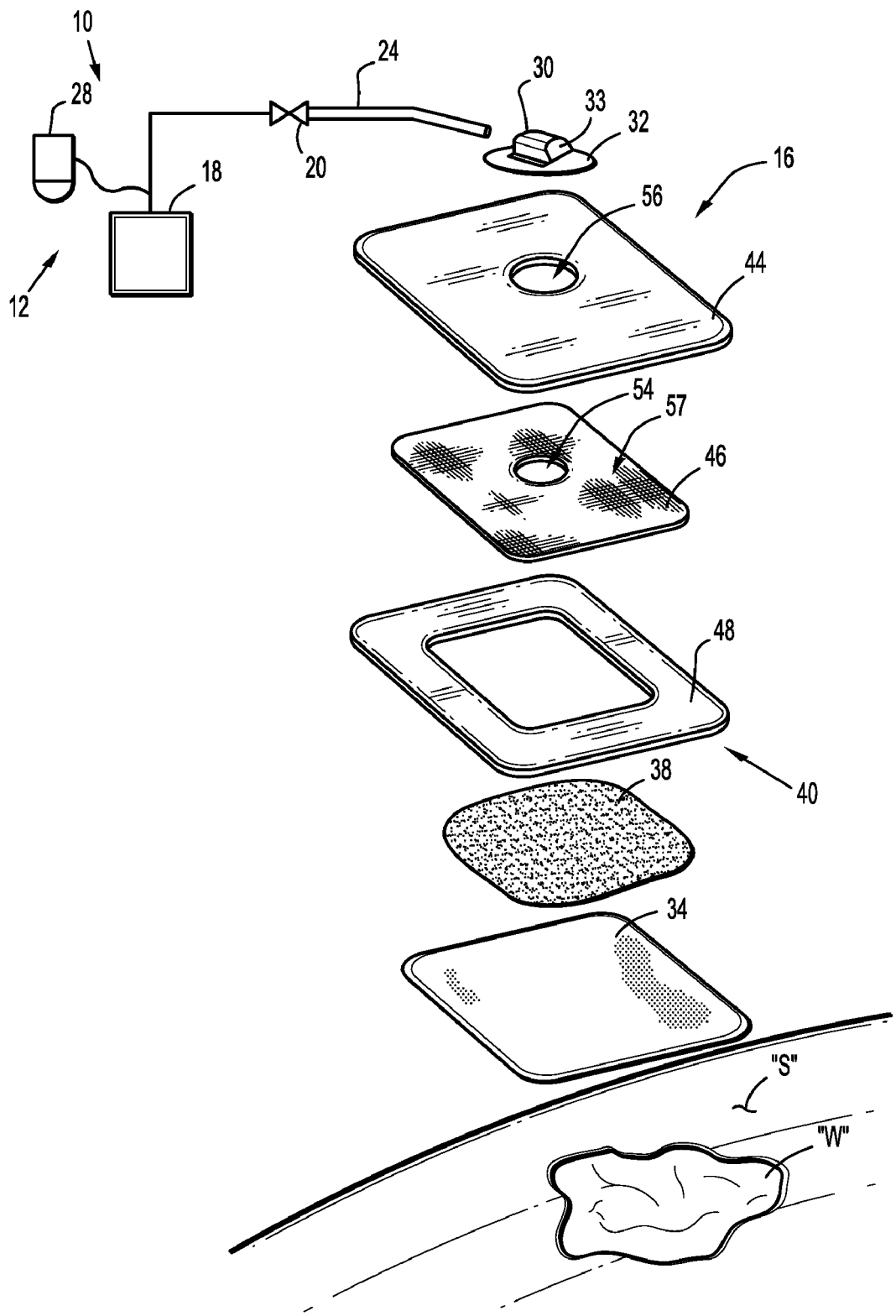
FIG. 1 is an exploded perspective view of a vacuum wound therapy system in accordance with the present disclosure.

The wound dressing of the present disclosure promotes healing of a wound by providing a reservoir over the wound where a reduced pressure may be maintained. The reservoir subjects the wound to a sub-atmospheric pressure to effectively draw wound fluid, including liquid exudates, from the wound without the continuous use of a vacuum pump. Hence, vacuum pressure may be applied once, or in varying intervals depending on the nature and severity of the wound. To facilitate fluid transport from the wound, a filler material may be included within the reservoir to promote the wicking of wound fluids subject to a reduced pressure. The use of a wound dressing in this manner has been found to promote healing by reducing the probability of infection, stimulating the deposition of granulation tissue and other beneficial processes. The wound dressing of the present disclosure includes a cover layer having a reinforcement structure to enhance the effect of a vacuum wound therapy treatment.

The attached figures illustrate exemplary embodiments of the present disclosure and are referenced to describe the embodiments depicted therein. Hereinafter, the disclosure will be described in detail by explaining the figures wherein like reference numerals represent like parts throughout the several views.

Referring initially to FIG. 1, a vacuum wound therapy system according to the present disclosure is depicted generally as 10 for use on a wound "w" surrounded by healthy skin "s." The vacuum wound therapy system 10 includes a vacuum system 12 in fluid communication with a vacuum reservoir 14 (FIG. 4A) defined by or within wound dressing 16. The vacuum system 12 includes a vacuum source 18 coupled to the dressing 16 through a one-way valve 20 and a vacuum tube 24. A collection canister 28 may be provided for wound drainage and debris. The vacuum system 12 is adapted to provide a reduced pressure to the vacuum reservoir 14 appropriate to stimulate healing of the wound "w." A more detailed description of an appropriate vacuum system 12 is found in commonly assigned U.S. Patent Application Publication 2007/0066946, the entire contents of which are incorporated herein by reference.

Figure 5:
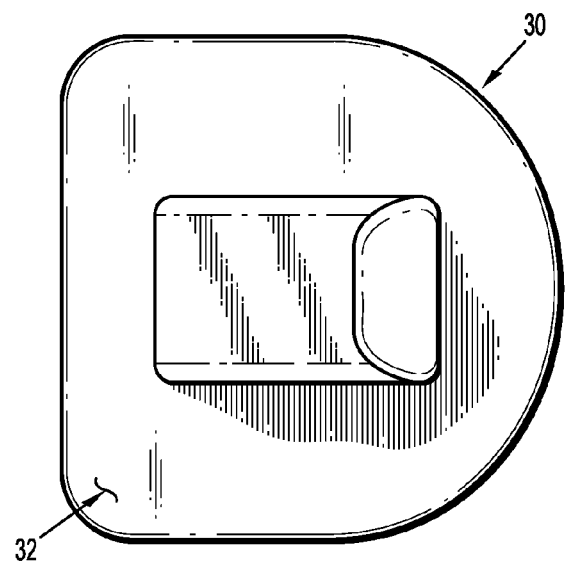
FIG. 5 is a top plan view of a vacuum port of FIG. 1.
Figure 6:
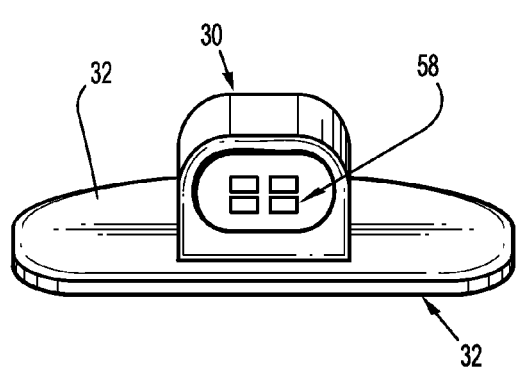
FIG. 6 is a perspective view of the vacuum port of FIG. 5.
Figure 7:
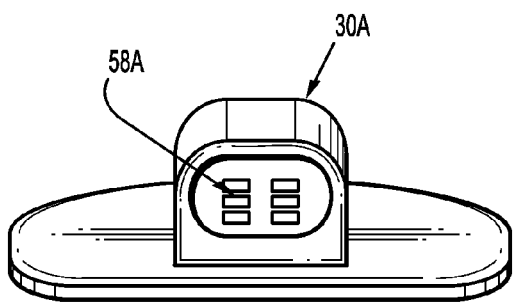
FIG. 7 is a perspective view of an alternative embodiment of a vacuum port.

A vacuum port 30, depicted in greater detail in FIG. 5 and FIG. 6, may also be included to facilitate connection of the vacuum system 12 to the dressing 16. The vacuum port 30 may be configured as a rigid or semi-rigid, low-profile component adapted to receive the vacuum tube 24 in a releasable and fluid-tight manner. The vacuum port 30 may be configured to include a wide and flexible flange 32 about its perimeter. The flange 32 permits an adhesive to be attached to either an underside of flange 32 for securement to an outer surface of cover layer 44, or to a top side of flange 32 to provide for mounting to the underside of the reinforcement layer 46. Either configuration provides a mechanism for connecting to the dressing 16. A hollow interior of the vacuum port 30 provides fluid communication between the vacuum tube 24 and the reservoir 14 defined by or within dressing 16. A connector segment 33 extends above the flange 32 for facilitating connection with the vacuum tube 24. It is envisioned that because of the possible intimate proximity of the vacuum port 30 to either reservoir 14 or wound filler 38, the performance of vacuum port 30 may be enhanced by the incorporation of a filter screen 58 as depicted in FIG. 6 and FIG. 7. Filter screen 58 may inhibit the migration of large particles that may otherwise be drawn into the vacuum port 30 and consequently create a restriction or blockage of the vacuum tube 24. The filter screen 58 may be integral to the configuration of the vacuum port 30 as part of the port flange 32. The filter screen 58 may include a number of openings, each smaller than a cross-sectional area of the vacuum tube 24 or the opening in the vacuum port 30 adapted to receive the vacuum tube 24, and collectively greater than the cross-sectional area of vacuum tube 24 or the opening in the vacuum port 30 adapted to receive the vacuum tube 24. For example, the filter screen 58 of vacuum port 30 may include four relatively large openings, while the filter screen 58A of vacuum port 30A depicted in FIG. 7 may include six relatively small openings. The openings in the filter screens 58, 58A are dimensioned to minimize the passage of tissue particles of a predetermined dimension through the respective vacuum port 30, 30A.

Figure 8:
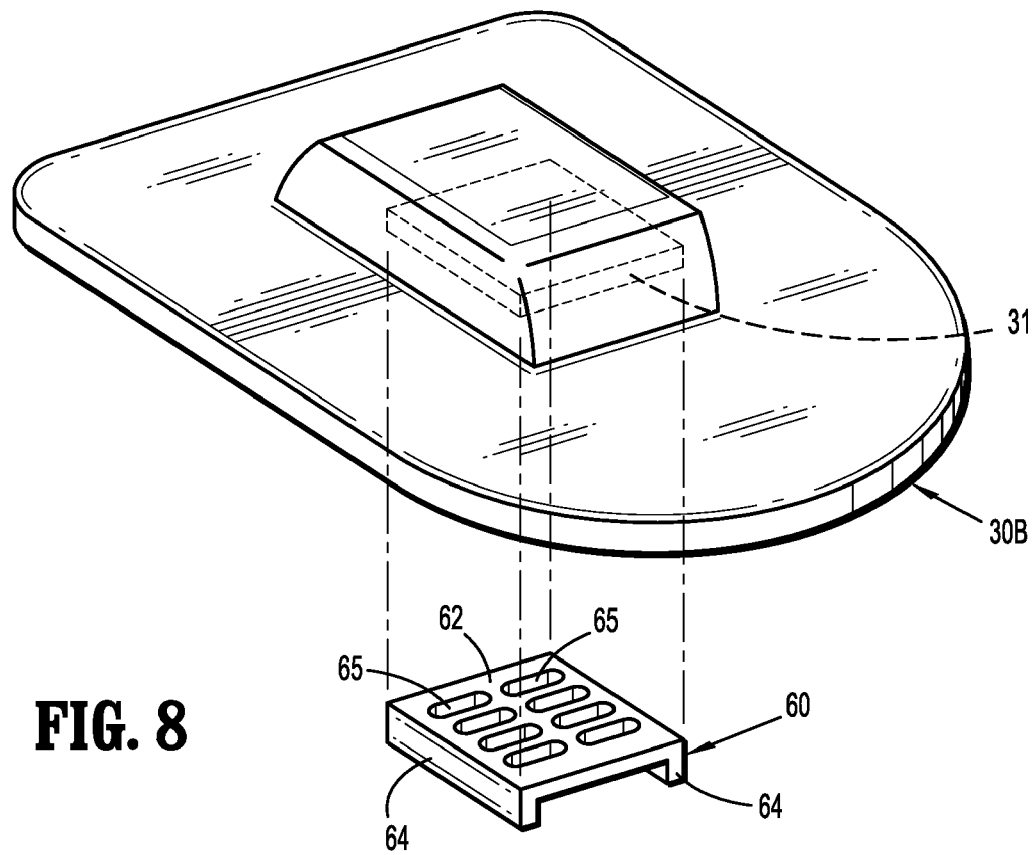
FIG. 8 is an exploded perspective view of an alternative embodiment of a vacuum port assembly including a portal member and an independent filter screen.
Figure 8A:
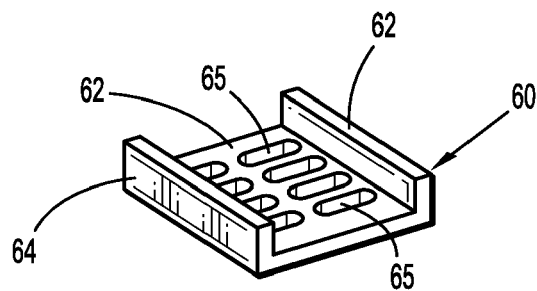
FIG. 8A is a perspective view of the filter screen of FIG. 8 in an alternate orientation.
Figure 8B:
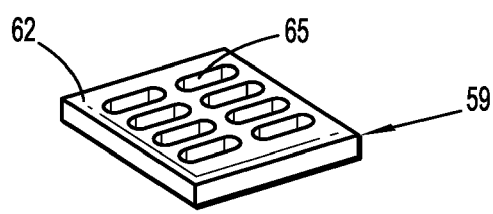
FIG. 8B is a perspective view of an alternate embodiment of an independent filter screen.
Figure 9:
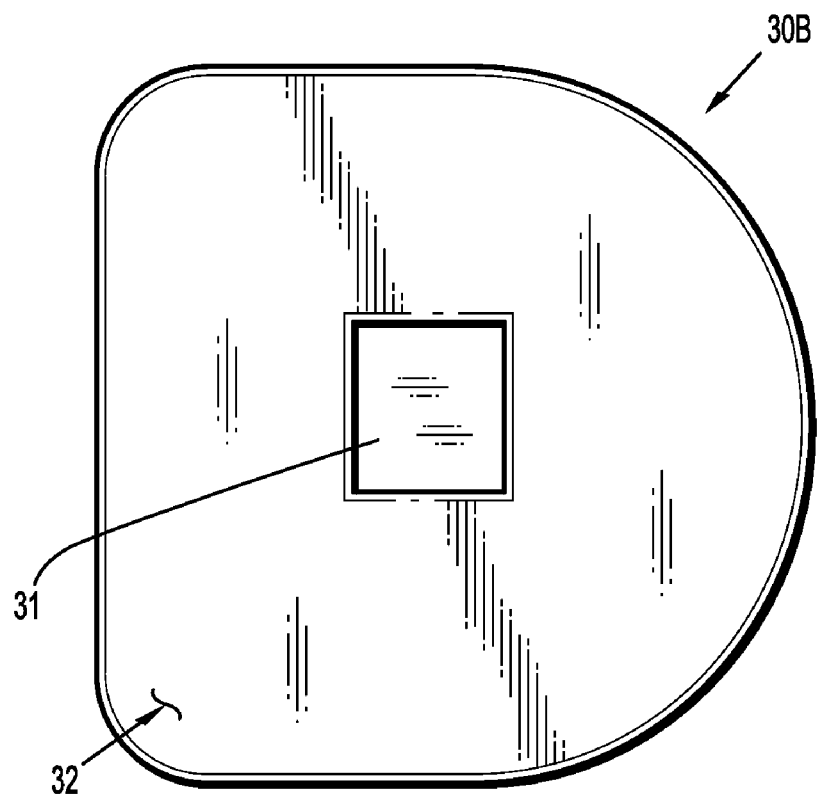
FIG. 9 is a bottom plan view of the portal member of FIG. 8.
Figure 10:
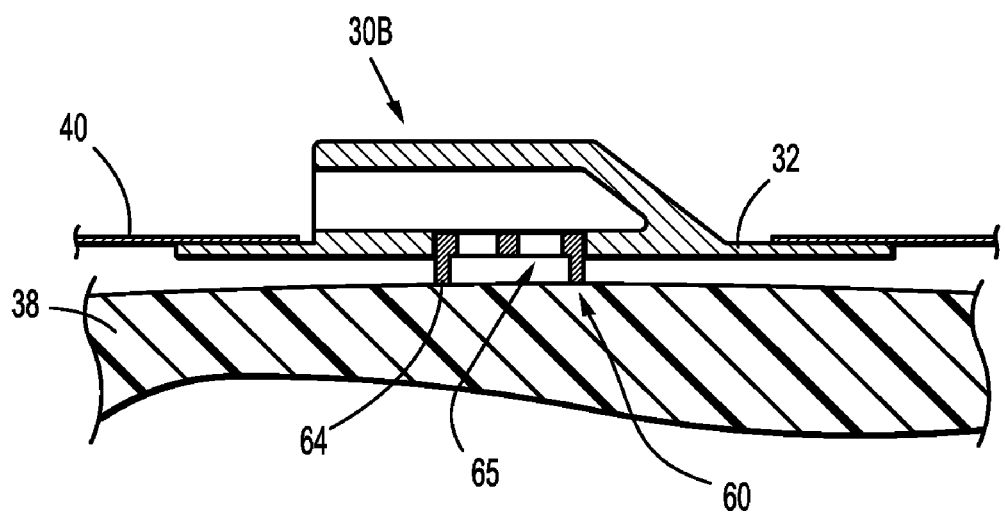
FIG. 10 is a partial cross sectional view of the vacuum port assembly assembled in a wound dressing.
Figure 11:
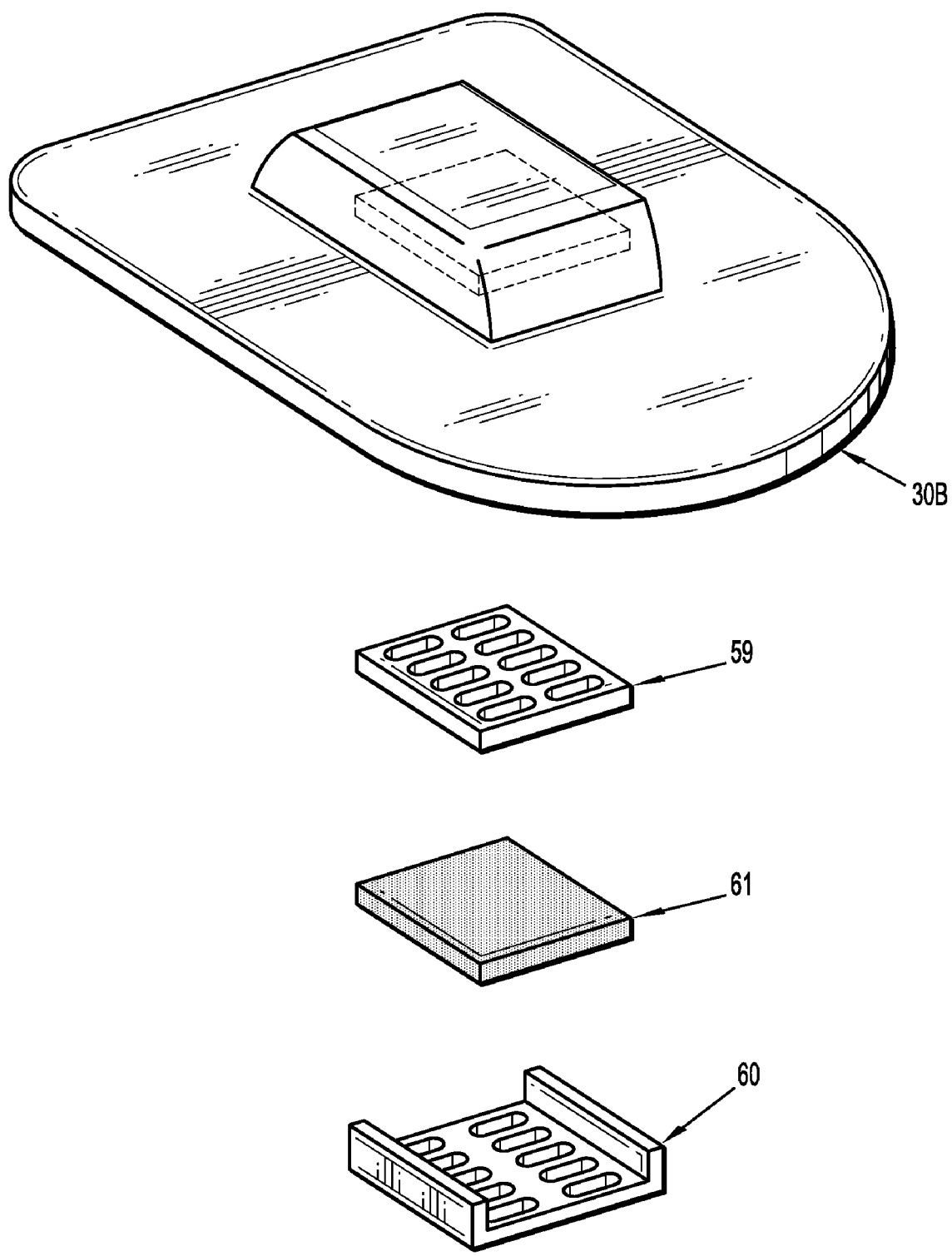
FIG. 11 is an exploded perspective view of an alternative embodiment of a vacuum port assembly including a treatment element.

Another alternate embodiment of a vacuum port is depicted generally as 30B in FIGS. 8, 9, 10 and 11. Vacuum port 30B may be configured to accept a filter screen 59 or 60 as a distinct or independently manufactured component as depicted in FIGS. 8, 10 and 11. An opening or cavity 31 depicted in the plan view of FIG. 9 and shown in phantom in FIG. 8 on an underside of vacuum port 30B may be adapted to permit filter screen 59 to be permanently bonded therein such that filter screen 59 is substantially flush with the underside of vacuum port 30B. Alternatively, filter screen 60 may be bonded to the opening on the underside of vacuum port 30B. Filter screen may 60 includes a generally flat base 62 through which the openings 65 extend, and a pair lips 64 projecting from the base 62 along opposite edges of the filter screen 60. The lips 64 may be dimensioned to be flush with a patient facing under surface of the flange when received within the cavity 31. Alternatively the lips 64 may extend beyond the under surface of the flange to extend beyond the cavity 31 in the portal member 30B as depicted in FIG. 10. Filter screen 60 may exhibit an increased surface area available for bonding within cavity 31 of vacuum port 30B. Filter screen 60 may be secured within cavity 31 by bonding, cements, adhesives or the like. In one embodiment, filter screen 62 is positioned within cavity 31 with lips 64 facing toward the wound (FIGS. 8 and 10). In another embodiment, filter screen 62 is positioned within lips 64 facing toward vacuum port 30B and away from the wound (FIG. 8A). In another embodiment, base 62 is devoid of lips 64 as shown in FIG. 8B, and is substantially planar.

It is also envisioned that filter screens 59 and 60 may be provided in combination with a treatment element 61 comprising a therapeutic material as depicted in FIG. 11. Treatment element 61 may be inserted between filter screens 59, 60 and may secured to vacuum port 30B by an appropriate adhesive bond. The treatment element 61 and filter screens 59, 60 may define an insert for reception into cavity or opening 31 on the underside of portal member 30B. This arrangement may provide a convenient method of treating the wound exudate as it is drawn from the wound "w." Treatment element 61 may comprise fibrous or granulated materials contained in a porous container or wrap to facilitate placement between filter screens 59 and 60. Treatment element 61 may include materials such as activated charcoal or other odor control or neutralizing substances. Treatment element 61 may include anti-bacterials such as polyhexamethylene biguanide (PHMB). Also, antimicrobials such as ionic metals or biguinides may be included to reduce the bio-burden of the exudate or microbials within the exudate as the exudate is drawn in to a collection canister 28. In the alternative, filter screens 59, 60 may comprise charcoal, antimicrobials, anti-odor substances.

Vacuum tube 30 may be configured to accept a variety of tubing geometries such as round, oblong or elliptical. Vacuum port 30 may be provided as a pre-affixed component of dressing 16, as part of vacuum system 12 or entirely independently. Also vacuum port 30 may not be necessary depending on the configuration of dressing 16.

Wound dressing 16 generally includes a contact layer 34, filler 38 and a reinforced cover layer 40. Reinforced cover layer 40 may be formed from a composite including a backing layer 44, a reinforcement layer 46 and an adhesive layer 48. Each layer of wound dressing 16 is described in greater detail below.

Contact layer 34 may be sufficiently conformable to be positioned in direct contact with an irregularly shaped surface of a wound bed "w." A thin film of polyethylene or other suitable non-adherent material may form the contact layer 34 to limit the adherence of filler 38 and other substances to the wound "w." Apertures or perforations in the film permit fluids to pass through the contact layer 34, allowing for the sub-atmospheric pressure to penetrate into the wound "w" and for exudates to flow freely out of the wound "w." By selecting an appropriate film material, the passage of wound exudate through contact layer 34 may be controlled so as to be substantially unidirectional to prevent wound exudate from flowing back into the wound. To promote a unidirectional flow, a conical apertured film, such as those provided by Tredegar Film Products of Richmond, Va., may be selected for forming contact layer 34. This type of film is arranged with apertures positioned at the peaks of cone shaped formations in the film material such that exudate encounters the film as an array of micro-funnels in one direction and an array of collecting basins in the other. Though it is depicted in a square configuration, the shape of the contact layer 34 can be customized to better suit the wound geometry. Unidirectional flow of exudates may also be promoted by the selection of other materials including a lamination of layers having varying absorptive characteristics. One exemplary material, which may be used as a contact layer is sold under the trademark XEROFLO® by Kendall Corp., a division of Covidien.

Figure 4A:
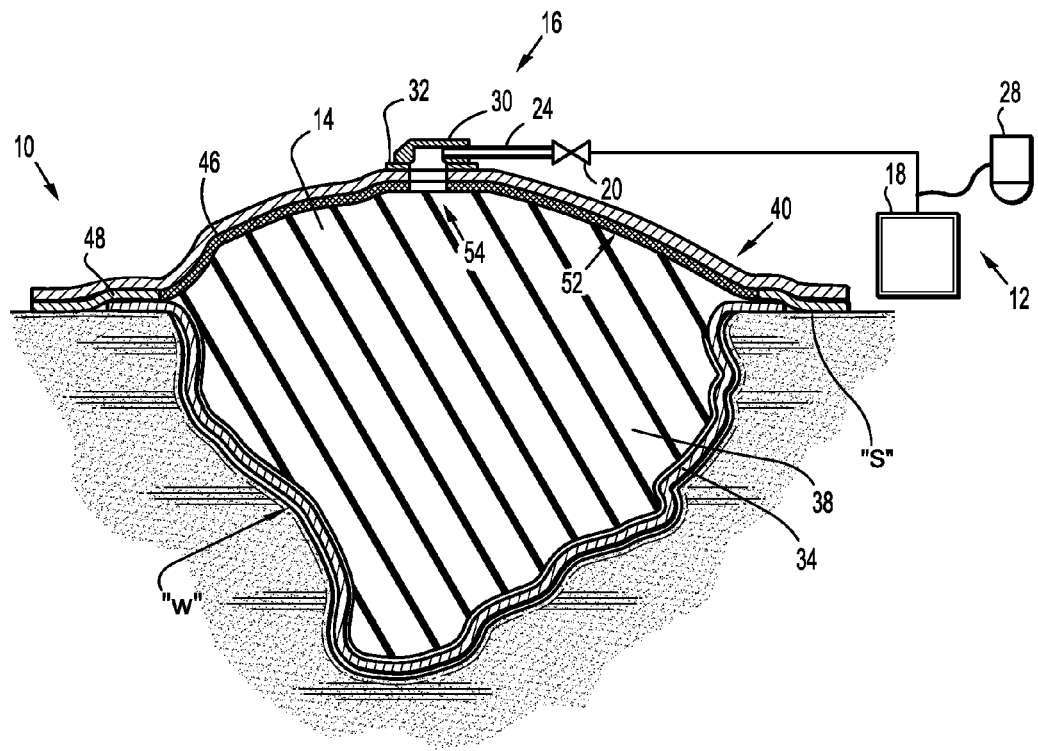
FIG. 4A is a cross sectional view of the vacuum wound therapy system of FIG. 1 installed over wound on a patient prior to application of a reduced pressure.

Filler 38 may be arranged over contact layer 34 to fill wound "w" to the level of the surrounding healthy skin "s" or may over-fill the wound "w" as depicted in FIG. 4A. An absorbent material such as non-woven gauze or reticulated foam may be used for filler 38 to trap or transport any exudate that migrates through contact layer 34. An antimicrobial dressing sold under the trademark KERLIX® by Kendall Corp., a division of Covidien, may be suitable for use as filler 38. To prevent adhesion to the wound "w," the filler 38 may also comprise a material configured such that any stray fibers do not tend to protrude through apertures of contact layer 34 where they may become engulfed by newly forming granulation tissue. One particular type of material exhibiting this characteristic is often referred to as "tow." The manufacturing process for synthetic fibers often includes an extrusion of an indeterminate length of continuous filaments, which are spun together to form fibers. It is the continuous lengths of un-spun filaments which are referred to as tow. A single length of tow formed from a hydrophobic material such as polyolefin may be laid in the wound bed "w" to form filler 38. This arrangement allows for a complete removal of filler 38 when the dressing 16 is changed without re-injuring the wound "w."

Figure 2:
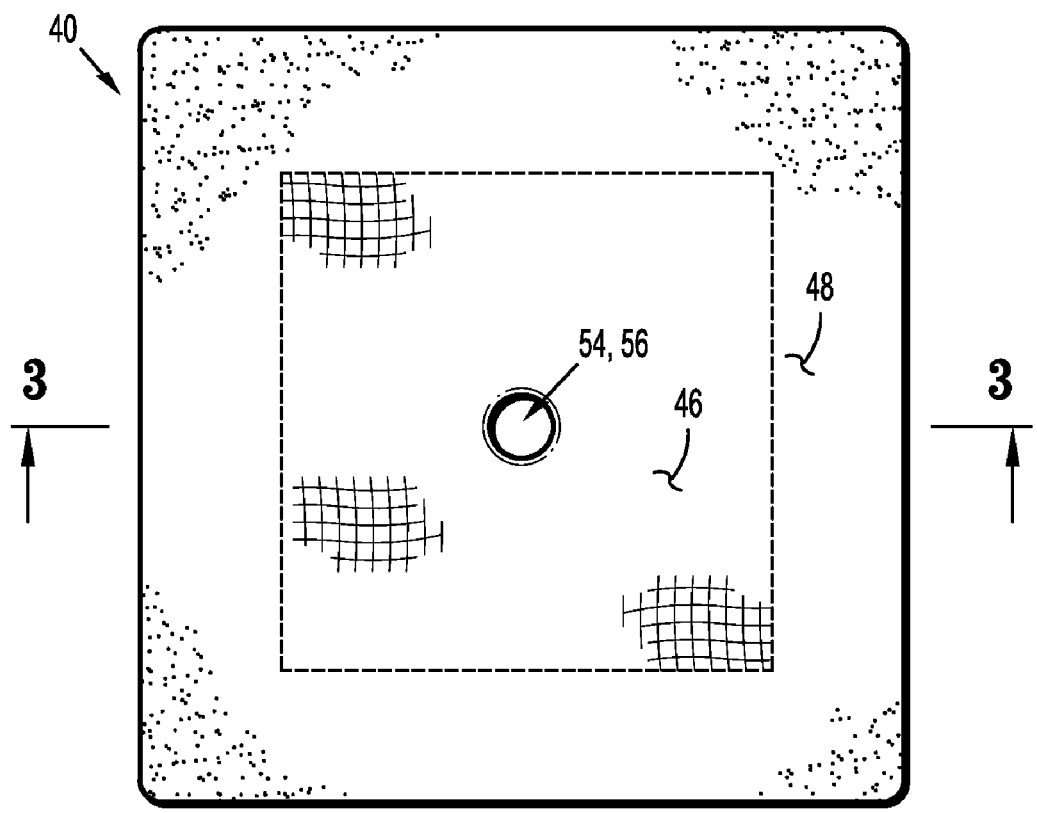
FIG. 2 is an orthographic view of a wound facing side of the cover layer of FIG. 1.

Cover layer 40 may be placed over the wound "w" enclosing the contact layer 34 and filler 38 therein. The periphery of cover layer 40 extends laterally beyond the perimeter of the wound bed "w" so as to contact the healthy skin "s" to form a seal over the wound "w." As depicted in FIG. 2, adhesive layer 48 may extend to the periphery of cover layer 40 to provide the seal with the use of a medical-grade, pressure-sensitive adhesive. The adhesive layer 48 may be adapted to provide a fluid-tight and bacteria-tight seal around a peripheral region of dressing 16 such that exudate cannot escape through the edges of the dressing 16 and external air and contaminants may not enter the wound area. To provide such a barrier, the adhesive layer 48 may, for example, be on the order of 1.0 to 10 mils thick depending on the adhesive used. In general, a high peal-strength adhesive may be used to resist inadvertent lift-off, roll or "flagging," i.e., a failure of the dressing to adhere to itself or the patient, at the edges of the cover layer 40. The adhesive defining the adhesive layer 48 may include, but is not limited to, medical grade acrylics, rubber base or silicone adhesives. Preferably, those adhesives included with the dressing sold under the trademark Polyskin II Transparent Dressings by Kendall Corp., a division of Covidien, may be used. Adhesive layer 48 forms a continuous band around the peripheral region of cover layer 40, but contains an opening such that the adhesive layer does not extend inwardly to the central areas of cover layer 40.

Figure 3:
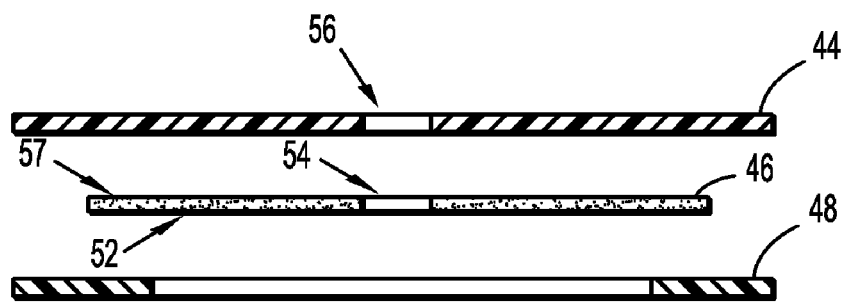
FIG. 3 is an exploded cross sectional view taken along the line 3-3 of FIG. 2.

As depicted in FIG. 3, reinforcement layer 46 may overlap adhesive layer 48 at an outer edge such that an outer periphery of reinforcement layer 46 is firmly affixed to backing layer 44. Reinforcement layer 46 extends to a peripheral region of cover layer 40, but not necessarily to an outer perimeter of the cover layer 40. Reinforcement layer 46, particularly any portion not overlapping the adhesive layer 48, may be affixed to backing layer 44 with a light coat of an adhesive 57 applied to the appropriate side of the reinforcement layer 46 or the backing layer 44. A portion of a wound facing side 52 of the reinforcement layer 46 carries no adhesive to prevent adhesion of the cover layer 40 to the filler 38. An aperture 54 extends through the reinforcement layer 46 to permit fluid communication between the reservoir 14 and vacuum system 12.

The reinforcement layer 46 may comprise a mesh of polyethylene terephtalate (PET) fibers, which offer good liquid resistance making it suitable for use in a moist wound environment. PET fibers may be used to form woven or non-woven reinforcements having large pore sizes. Some PET reinforcement manufacturing methods provide for interlinking the fiber junctions to yield a mesh that is flexible in multiple directions and also does not unravel when cut. One such method is known as hydro-entanglement. PET reinforcements thus manufactured tend to have a high shear stiffness that may be useful in reinforcing cover layer 40. One exemplary material, which may be suitable for incorporation into reinforcement layer 46, is sold under the trademark Sontara® by DuPont. Alternatively, reinforcement layer 46 may be formed from another reinforcement or mesh structure having suitable shear stiffness. Examples of suitable structures include extruded netting and apertured films. Suitable materials for use in such alternate structures include PET, polyethylene, nylon and polypropylene. Additionally, woven structures may be used for reinforcement layer 46. Acceptable woven materials may include cotton gauze, woven acetate and nylon.

Extending to the periphery of the cover layer 40 is backing layer 44. Backing layer 44 provides a substrate to which reinforcement layer 46 and adhesive layer 48 may be affixed. An aperture 56 extends through the backing layer 44 to permit fluid communication between the reservoir 14 and vacuum system 12. Backing layer 44 may be formed from a flexible polymeric membrane to serve as a fluid barrier to allow for a sub-atmospheric pressure to be established in vacuum reservoir 14, and also as a microbial barrier preventing contaminants from entering the wound area. For example, backing layer 44 may comprise a polyurethane film having a thickness from about 0.8 mils to about 1.0 mil. Preferably, the backing layer 44 is formed from a moisture vapor permeable membrane to promote the exchange of oxygen and moisture vapor between the wound site and the atmosphere. One exemplary material is a transparent membrane sold under the trade name POLYSKIN® II by Kendall Corp., a division of Covidien. Other materials which may be suitable for use in a backing layer include the thin films marketed under the names TEGADERM™ by 3M of St. Paul, Minn. and OPSITE™ by Smith and Nephew PLC of London, UK. Reinforcement layer 46 may be configured so as not to impede the transmission of moisture vapor by including, for example, a large pore size.

Figure 4B:
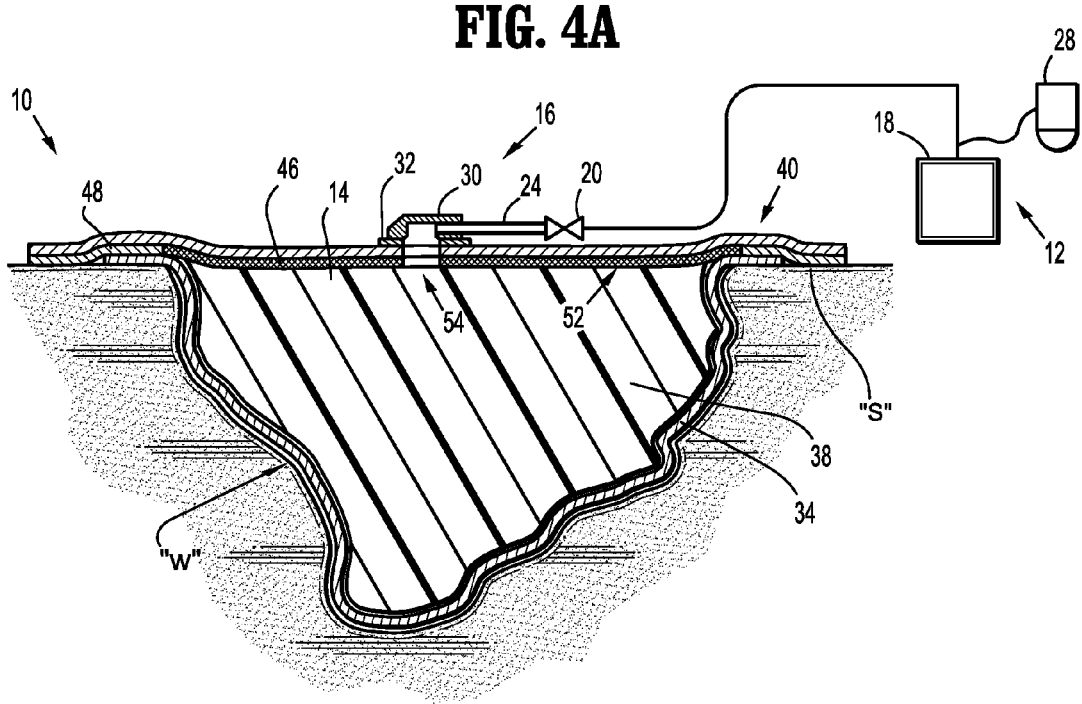
FIG. 4B is a cross sectional view of the vacuum wound therapy system of FIG. 1 installed over wound on a patient following an application of a reduced pressure.

As seen in FIG. 4A, reservoir 14 is defined by or within wound dressing 16 when applied to the skin. Filler 38 may be included to fill the reservoir 14. Evacuating atmospheric gasses from the reservoir 14 may impart a tendency for cover layer 40 to flatten against the wound "w" as depicted in FIG. 4B. This tendency of cover layer 40 to deform may draw the peri-wound margins into the wound "w" and put the surrounding skin "s" in tension. This tendency may be counteracted or resisted by the shear stiffness in reinforcement layer 46 such that the cover layer 40 may better main its shape. Because reinforcement layer 46 extends to a peripheral region of cover layer 40 and backing layer 44 anchored to healthy skin "s," the forces associated with evacuating reservoir 14 may be transferred beyond the perimeter of the wound "w," and may be manifested as compression forces. Thus reinforcement layer 46 reinforces cover layer 40 and vacuum reservoir 14.

A central region of reinforcement layer 46 may be devoid of an adhesive coating, such that the reinforcement layer 46 may not tend to adhere to or disturb filler 38, particularly as the reduced pressure is removed from reservoir 14. Reinforcement layer 46 thus further protects wound "w" to promote healing throughout the evacuation cycles of a VWT procedure.

Although the foregoing disclosure has been described in some detail by way of illustration and example, for purposes of clarity or understanding, it will be obvious that certain changes and modifications may be practiced within the scope of the appended claims.

What is claimed is:

1. A wound dressing for use in a vacuum wound therapy treatment comprising:
   a cover layer configured for positioning over a wound to define a reservoir in which a reduced pressure may be maintained over the wound;
   a portal member mounted to the cover layer, the portal member defining a fluid passage for fluid coupling with a reduced pressure supply conduit for creating the reduced pressure within the reservoir; and
   a filter screen integral to the portal member and mounted relative to the fluid passage, the filter screen dimensioned to minimize passage of tissue particles of predetermined dimension through the fluid passage of the portal member.

2. The wound dressing according to claim 1, wherein the filter screen comprises a therapeutic material, the therapeutic material adapted to control a characteristic of exudate drawn through the fluid passage of the portal member.

3. The wound dressing according to claim 2, wherein the therapeutic material includes activated charcoal to control an odor of the exudate.

4. The wound dressing according to claim 2, wherein the therapeutic material includes an antimicrobial to control a bio-burden of the exudate.

5. The wound dressing according to claim 1, including a treatment element mounted adjacent the filter screen, the treatment element comprises a material adapted to control a characteristic of exudate drawn through the fluid passage of the portal member.

6. The wound dressing according to claim 5 wherein the material of the treatment element is adapted to control one of odor and microbials.

7. The wound dressing according to claim 1 wherein the portal member includes:
   a flange defining an outer surface and a patient surface generally facing the wound, the fluid passage extending through the outer surface and the patient surface; and
   a connector segment for connection to the reduced pressure supply conduit.

8. The wound dressing according to claim 7 wherein the flange of the portal member is secured to the cover layer.

9. The wound dressing according to claim 1 including a negative pressure source in fluid communication with the reduced pressure supply conduit.

10. The wound dressing according to claim 1, wherein the filter screen extends across the fluid pass age of the portal member such that any fluid passing through the fluid passage of the portal member must pass through the filter screen.

11. A wound dressing for use in a vacuum wound therapy treatment comprising:
   a cover layer for positioning over a wound to define a reservoir in which a reduced pressure may be maintained over the wound;
   a portal member mounted to the cover layer, the portal member defining a fluid passage for fluid coupling with a reduced pressure supply conduit for creating the reduced pressure within the reservoir, the portal member including an opening adapted to receive a vacuum tube in a releasable and fluid tight manner; and a filter screen integral to the portal member and mounted such that a base of the filter screen extends across an entire face of the fluid passage, the filter screen including a plurality of distinct openings extending directly through the base in a direction of fluid flow through the portal member, the openings dimensioned to reduce passage of tissue particles of predetermined dimension through the fluid passage of the portal member wherein each of the distinct openings extending through the base of the filter screen exhibits a cross-sectional area smaller than a cross-sectional area of the opening adapted to receive the vacuum tube, the distinct openings collectively exhibiting a cross-sectional area greater than the cross-sectional area of the opening adapted to receive the vacuum tube.

12. The wound dressing according to claim 11, wherein the filter screen includes a pair of lips projecting from opposite edges of the base.

* * * * *